United States Patent [19]

Samour

[11] Patent Number: 5,620,980
[45] Date of Patent: Apr. 15, 1997

[54] METHOD FOR TREATING HAIR LOSS

[75] Inventor: Carlos M. Samour, Newport, R.I.

[73] Assignee: MacroChem Corporation, Lexington, Mass.

[21] Appl. No.: 392,231

[22] Filed: Feb. 22, 1995

[51] Int. Cl.$^6$ .................. A61K 31/505; A61K 31/335
[52] U.S. Cl. .................... 514/256; 514/452; 514/467
[58] Field of Search ........................ 514/256, 452, 514/467

[56] References Cited

U.S. PATENT DOCUMENTS

| | | |
|---|---|---|
| 4,085,222 | 4/1978 | Rhodes et al. . |
| 4,139,619 | 2/1979 | Chidsey, III et al. . |
| 4,596,812 | 6/1986 | Chidsey, III et al. . |
| 4,861,764 | 8/1989 | Samour et al. . |

FOREIGN PATENT DOCUMENTS

| | | |
|---|---|---|
| 2078732 | 1/1982 | United Kingdom . |
| 9216236 | 10/1992 | WIPO . |

OTHER PUBLICATIONS

Diani, et al., Skin Pharmacology (Mar. 1994).
Capozza, Chemical Abstracts, 88:513558x (1978).
Schaefer, et al., Chemical Abstracts, 97:38946d (1982).
Friedman, R., "Upjohn Enhances Hair Regeneration", Bio-World Today, p. 2 (Sep. 5, 1991).
Marty, et al., "Dioxolane Derivatives: A New Class of Percutaneous Absorption Enhancer", Center for Bio-Pharmaceutical Sciences, (1989).
Chew, et al. (1993), Abstract for the IIS, Sixth Central US Meeting, May 13–14, 1993.
Slatter, et al. (1993), Abstract for the ISSX Sep. 1993 Meeting.
MacroChem Press Release, May 6, 1994.
MacroChem Press Release, Oct. 8, 1992.

*Primary Examiner*—Zohreh Fay
*Attorney, Agent, or Firm*—Sherman and Shalloway

[57] ABSTRACT

The combination of minoxidil and 2-n-nonyl-1,3-dioxolane is effective in promoting hair growth when applied once daily.

1 Claim, 1 Drawing Sheet

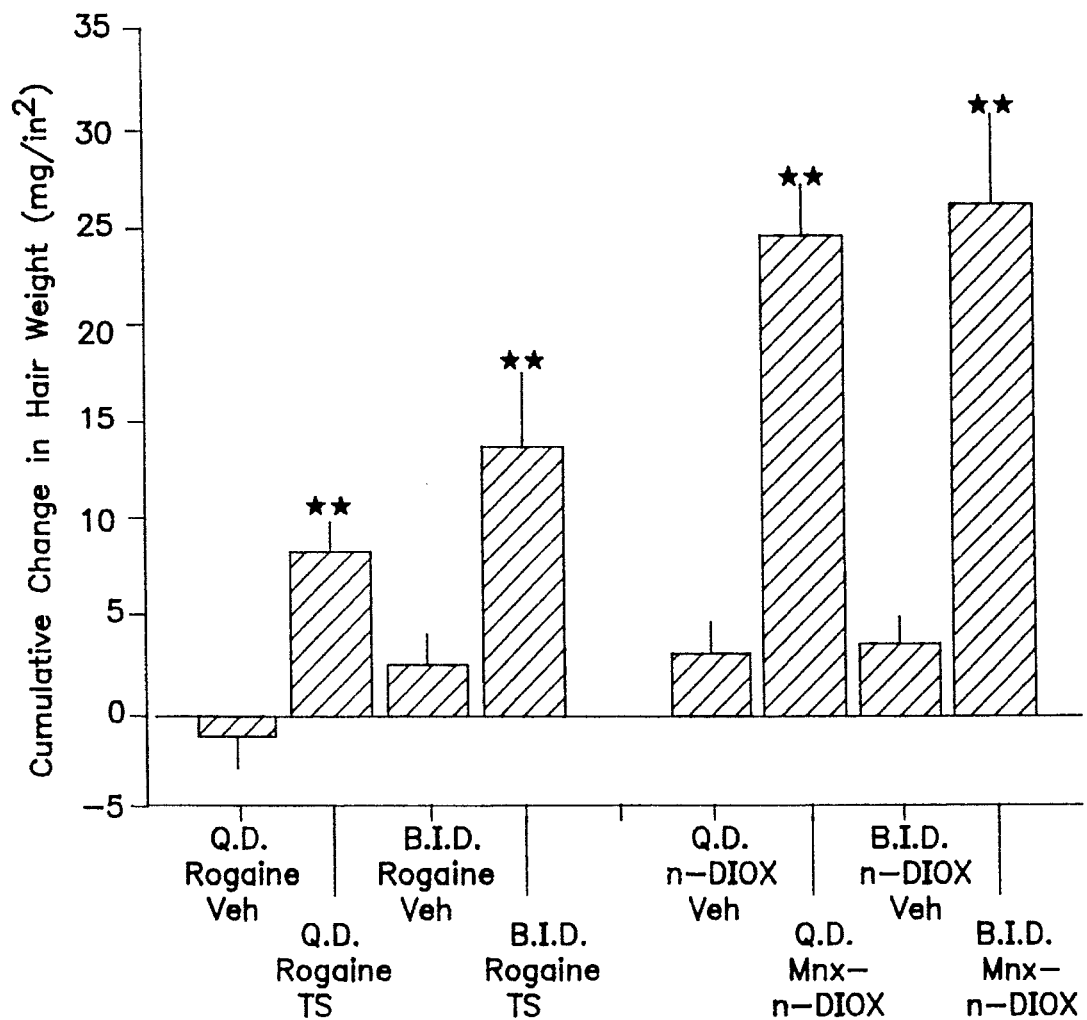

METHOD FOR TREATING HAIR LOSS

FIELD OF THE INVENTION

This invention relates to a method of treating hair loss by topical application to skin of a composition containing minoxidil, wherein the composition exhibits improved penetration and efficacy of the minoxidil contained therein, thereby decreasing the amount of minoxidil and number of applications of minoxidil required to obtain hair regrowth. In particular, the invention relates to a method of treating hair loss by the once daily application of a composition containing minoxidil and a skin penetration enhancer that increases the topical absorption of minoxidil.

BACKGROUND OF THE INVENTION

In recent years a number of compounds for the treatment of hair loss have been developed, including minoxidil (Rogaine®). Hair loss treatment with such compounds is generally provided by delivery of the active ingredient or ingredients through the skin, i.e. transdermally, as opposed to other methods of parenteral administration. The large surface area of the skin and the extensive circulatory and lymphatic networks available near the skin surface make topical application of drugs for treatment of hair loss extremely desirable. Moreover, topical application of drugs is relatively non-invasive, convenient, proven to be safe and provides greater control over delivery of active agents to the desired target site.

However, in order to be effective, an active agent for hair treatment must pass through the outer layer of skin or epidermis and into the dermis layer before being absorbed into the bloodstream. The epidermis comprises two main parts, the stratum corneum and the stratum germinativum. The stratum corneum forms the outermost layer of the epidermis and consists of many stratified layers of compacted, flattened, keratinized cells which have lost their nuclei. This outermost layer serves as a physical barrier to microorganisms and most chemical agents. In particular, it behaves as a primary barrier to percutaneous absorption of drugs. Because of the barrier effect of the skin, it has heretofore only been possible to deliver drugs that are "low-dose" drugs, i.e. in the range of 15 mg/day or less, or those of low molecular weight. In addition, drugs for transdermal delivery must have the proper lipophilic-hydrophilic balance to permit adequate absorption. As early as the beginning of this century it has been known that lipid-soluble substances, such as non-electrolytes have a comparatively greater skin permeability than water-soluble substances, such as electrolytes.

Percutaneous absorption or transdermal permeation is basically a composite of a series of steps in sequence. A penetrant molecule is first absorbed onto the surface layers of the stratum corneum, diffuses through the stratum corneum and the viable epidermis below, and finally diffuses through the papillary dermis and into the microcirculation.

Diffusional resistance of the stratum corneum to topically applied agents has been demonstrated with various drugs. In order to overcome this barrier effect a number of compounds have been developed which enhance the transdermal delivery of drugs, such as dimethyl sulfoxide (DMSO), polyethylene glycol monolaurate, alkyl lactams, long chain amides, and substituted 1,3-dioxacyclopentanes and substituted 1,3-dioxacyclohexanes. For example, U.S. Pat. No. 3,551,554 discloses DMSO, U.S. Pat. No. 3,989,816 discloses 1-substituted azacycloheptane-2-one, U.S. Pat. No. 4,132,781 discloses a topical antibiotic composition containing 2-pyrrolidone or an n-lower alkyl-2-pyrrolidone, U.S. Pat. No. 4,017,641 discloses propylene glycol and 2-pyrrolidone-containing compositions and U.S. Pat. No. 4,861,764 discloses 1,3-dioxolane and 1,3-dioxane derivatives as percutaneous absorption enhancers. WO 92/16236 discloses methods and compositions for enhancing the rate of absorption of topically administered physiologically active compounds. Minoxidil is disclosed as one of these compounds. The penetration enhancers are amino alcohol derivatives which may form a 1,3-dioxane ring.

Therapy of age related hair loss in androgenic alopecia patients with topical solutions of minoxidil (Rogaine®) alone, or in combination with skin penetration enhancers, such as DMSO, has resulted in only moderate to dense regrowth of hair in less than 40% of such patients (Katz, H. I., Clin. Dermatol., 6:195–199, 1988). Moreover, treatments with topical solutions of minoxidil require multiple applications of the active ingredient each day, which can be very inconvenient as well as expensive. Androgenic alopecia or common baldness represents 99 percent of all cases of hair loss (Brodland and Muller, Cutis, 47:173–176, 1991) and, therefore, there is a need for improved compositions and methods for treating hair loss in patients with age related baldness. In particular, there is a need for methods of treating hair loss that require fewer applications of active ingredient, e.g. minoxidil, and which will also provide hair regrowth sooner, in more abundance, and thicker, than is presently observed using minoxidil and known penetration enhancers.

It is therefore, an object of the present invention to provide a treatment for hair loss that is safe, simple, easy to apply, and inexpensive when compared to other hair loss treatments.

It is also an object of the present invention to provide a treatment for hair loss that provides faster and more abundant hair regrowth than conventional treatments, using fewer applications of minoxidil and using the same concentration of minoxidil per treatment as is conventionally used.

SUMMARY OF THE INVENTION

The present invention relates to an improved method for treating hair loss, the improvement being topically applying once per day to skin at a desired area for hair regrowth minoxidil and a non-toxic, effective amount of a 1,3-dioxacycloalkane penetration enhancing compound as previously disclosed in my issued U.S. Pat. No. 4,861,764 and having the following formula (I)

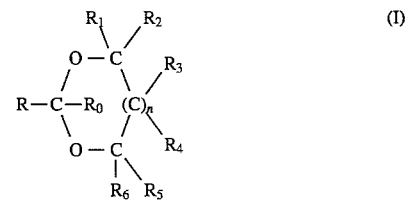

wherein each of R, $R_0$, $R_1$, $R_2$, $R_3$, $R_4$, $R_5$ and $R_6$ is independently selected from hydrogen, $C_1$ to $C_{18}$ aliphatic groups, and substituted $C_1$ to $C_{18}$ aliphatic groups, wherein at least one of said R groups is a $C_4$ to $C_{18}$ alkyl group or $C_4$ to $C_{18}$ alkenyl group; the total number of carbon atoms in all of said R groups being no more than 40; and n is 0 or 1.

The present invention also relates to a composition for topical application to the scalp for promoting hair regrowth. The composition includes a 1,3-dioxacycloalkane of formula (I), minoxidil and cosmetic carriers comprising isopropanol and propylene glycol. This composition containing, for example, from about 2 to about 6% by weight minoxidil and from about 5 to about 20% by weight of a compound of formula (I), particularly 2-n-nonyl-1,3-dioxolane, is effective when applied in a single daily application over a course of time.

BRIEF DESCRIPTION OF THE DRAWINGS

FIG. 1 is a bar graph showing the cumulative change from base line of shaved scalp hair weight of monkeys treated by the present method and control monkeys.

DETAILED DESCRIPTION OF THE INVENTION

In an effort to improve the efficacy of topical minoxidil compositions for the treatment of hair loss, a more effective method for applying minoxidil and transporting it across the skin barrier has been developed. The present method requires fewer applications of minoxidil per day i.e., once per day treatment, and provides for faster and more effective hair regrowth than twice daily applications of the same amount of minoxidil using typical penetration enhancers including commercial minoxidil products. The method involves the alteration of the stratum corneum by application of a percutaneous absorption and penetration enhancing effective amount of an enhancing agent to the skin to permit greater delivery of minoxidil across the skin barrier, thereby reducing the number of applications of minoxidil required for hair regrowth, from multiple applications to only once a day application. It was quite unexpected to find a penetration enhancing agent which would allow minoxidil to be as effectively applied as or even more effectively applied once daily than conventional treatments requiring multiple daily applications. Moreover, it was equally unexpected to find a penetration enhancing agent which allowed minoxidil to effect hair regrowth after a shorter period of treatment than conventional treatments.

The enhancing agent is a 1,3-dioxacycloalkane (1,3-dioxolane or 1,3-dioxane) compound having at least one aliphatic group substituent having four to eight carbon atoms. The substituted 1,3-dioxolanes and 1,3-dioxanes have the formula (I)

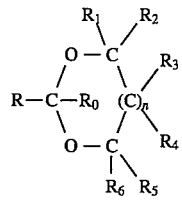

(I)

wherein the groups R, $R_0$, $R_1$, $R_2$, $R_3$, $R_4$, $R_5$, and $R_6$ are each independently selected from hydrogen and $C_1$ to $C_{18}$ aliphatic groups, (preferably alkyl or alkenyl), and the halo, hydroxy, carboxy, and carboalkoxy substituted forms thereof, with at least one of said groups being an alkyl or alkenyl group of $C_4$ to $C_{18}$, and n is 0 or 1; the total number of carbon atoms in all of said groups being no more than 40, and preferably less than 20 and not more than one thereof containing 18 or more carbon atoms.

In preferred compounds of formula (I) R is an aliphatic group of $C_4$ to $C_{18}$, more preferably $C_6$ to $C_{12}$ and most preferably, $C_7$ to $C_{10}$, and $R_0$ is hydrogen.

The general formulae representing the most preferred enhancers used in the present method are the following formula (II); formula (III) and formula (IV):

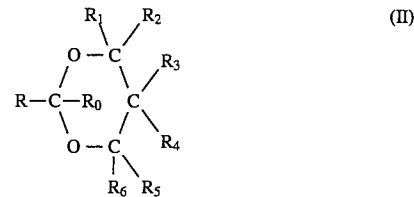

wherein R is an aliphatic group of $C_4$ to $C_{18}$ and preferably, $C_6$ to $C_{12}$ and most preferably, $C_7$ to $C_{10}$. The other groups ($R_0$, $R_1$, $R_2$, $R_3$, $R_4$, $R_5$ and $R_6$) are preferably selected from hydrogen or lower alkyl moieties ($C_1$ to $C_4$), however other groups, such as, for example, hydrogen, halo, carboxy, carboalkoxy and hydroxy may also be present;

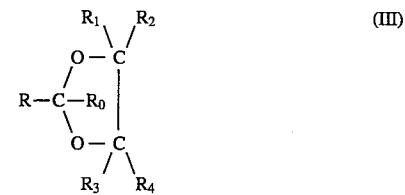

wherein R is $C_4$ to $C_{18}$, aliphatic group, preferably $C_6$ to $C_{12}$, and more preferably, $C_7$ to $C_{10}$ and the other groups are as described in formula (II);

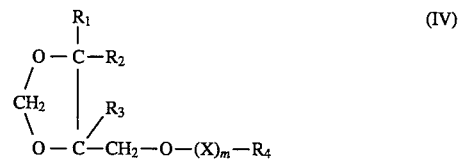

wherein $R_4$ is a $C_4$ to $C_{18}$ aliphatic group, preferably $C_6$ to $C_{12}$, and more preferably $C_7$ to $C_{10}$; and $R_1$, $R_2$, and $R_3$ are as described in formulas II and III; m is 0 or 1; and when m is 1, X is carbonyl

(—C—).

In formulas (II) and (III), it is preferred that $R_0$ is hydrogen.

The dioxane and dioxolane enhancer compounds used in the present method for treating hair loss include, for example, 2-n-pentyl-1,3-dioxolane, 2-n-heptyl-1,3-dioxolane, 2-n-nonyl-1,3-dioxolane, 2-n-undecyl-1,3-dioxolane, pentylene-1,5-bis-1,3-dioxolane, 2-(2', 6'-dimethyl-2,6-heptadienyl)-1,3-dioxolane, 2-(2', 6'-dimethyl-2-heptaenyl)-5-chloromethyl-1,3-dioxolane, 2-(2', 6'-dimethyl-2-heptaenyl)-5-chloromethyl-1,3-dioxolane, 2-(2', 6'-dimethyl-2,6-heptadienyl-)-5-chloromethyl-1,3-dioxolane, 2-(2', 6'-dimethyl-2,6-heptadienyl)-5-hydroxymethyl-1,3-dioxolane, 2-(2', 6'-dimethyl)-2-heptadienyl)-5-hydroxymethyl-1,3-dioxolane, 2-n-nonyl-1,3-dioxane, 2-n-undecyl-1,3-dioxane, 2-(2', 6'-dimethyl(2-heptaenyl)-1,3-dioxane, 2-(2', 6'-dimethyl-2-heptaenyl)-1,3-dioxane, 2-(2', 6'-dimethyl-2,6-heptadienyl)-5-(bis-ethylcarboxylate)-1,3-dioxane, 2-n-nonyl-5-(bis-ethylcarboxylate)-1,3-dioxane, 2-n-pentyl-5 -(bis-ethylcarboxylate)-1,3-dioxane, 2-(2', 6'-dimethyl-2-heptaenyl)-5-(bis-ethyl-carboxylate)-1,3-dioxane. 2-n-nonyl-1,3-dioxolane and 2-n-nonyl-1,3-dioxane are preferred, and the dioxolane is especially preferred.

Minoxidil (as described in U.S. Pat. Nos. 4,139,619 and 4,596,812, the disclosures of which are incorporated herein in their entirety by reference thereto) is 6-(1-piperidinyl)-2, 4-pyrimidinediamine-3-oxide.

The dioxacycloalkane compounds used in the present method for treating hair loss may be applied simultaneously with application of minoxidil, e.g., in admixture therewith or may be applied prior to or after treatment of the skin with minoxidil. In the present method, the dioxacycloalkane compound may be applied up to about 4 hours prior to or post treatment with minoxidil, but preferably for convenience within 1 hour prior to or post minoxidil treatment, more preferably within about 15 minutes of treatment with minoxidil and most preferably and conveniently, simultaneously therewith, and preferably, in admixture therewith.

The dioxane or dioxolane enhancer compound, alone or in combination with minoxidil and any pharmaceutically acceptable additives may be incorporated into any pharmaceutically acceptable formulation. However, the formulation should be substantive to the scalp, i.e., will not run off the scalp. Therefore, the preferred compositions are in the form of gels, ointments or creams, where the active ingredients may remain at the site of application for extended period of time, generally from about 30 minutes to about 6 hours being sufficient, more preferably for at least about 1 hour and up to about 4 hours.

Suitable additives that may be admixed with the dioxane or dioxolane enhancer compound and/or minoxidil include, but are not limited to solvents, such as water, glycols, esters, alcohols, lipid materials, coloring agents, fragrances, antioxidants, thickening agents, anti-oxidants, ultra-violet light stabilizers, preservatives, and other pharmaceutically accepted additives.

Minoxidil and the absorption enhancer dioxacycloalkane compound are, preferably, formulated into a single composition for simultaneous application to the skin.

The selection of additives may impact on the effectiveness of the composition. A particularly preferred safe and effective composition is based on a cosmetic carrier wherein a solvent system is an aqueous alcoholic solution containing ethanol, propanol or isopropanol, together with a lower alkyl ($C_1$–$C_4$) glycol, such as ethylene glycol or propylene glycol and, usually, a thickener or gelling agent. Another, often useful additive is dimethicone or other volatile silicone solvent and carrier.

Thus, a particularly preferred composition effective for promoting hair growth, even when applied in a once per day treatment, includes the following ingredients in the following amounts (weight percent)

|  | broad | intermediate | preferred |
|---|---|---|---|
| Minoxidil | 0.05–5% | 0.5–5 | 0.5–3 |
| Penetration enhancer | 0.2–25 | 0.5–15 | 2–15 |
| Water | 0–40 | 0 or 5–30 | 0 or 5–25 |
| Lower Alcohol | 0–90 | 5–60 | 10–60 |
| Lower glycol | 0–98 | 5–60 | 10–60 |
| Thickening agent | 0–5 | 0–3 | 0.1–2 |

Suitable formulations for topical applications to the skin are as follows:

Formula 1

Propylene glycol 97.5%

Carbopol 940 (B. F. Goodrich) 2.5%

Minoxidil and 2-n-nonyl-1,3-dioxolane were added to propylene glycol under agitation. Carbopol 940 was then added to the resulting solution under vigorous mixing conditions to provide a gel.

Formula 2

Isopropyl myristate 82.0%

Tween 80 10.0%

Aerosil R 972 8.0%

Formula 3

Propylene glycol 89.0%

Water 10.0%

Carbopol 940 0.5%

Triethanolamine 0.5%

Formula 4

Propylene glycol 50.0%

Alcohol (95%) 50.0%

Formula 5

Propylene glycol 50.0%

Alcohol 30.0%

Water 20.0%

Each of the foregoing formulae may serve as a suitable base for both the minoxidil and the absorption enhancer compounds used in the present method.

Generally, an amount of about 100 µl to 2 ml per 100 square centimeters of skin, and preferably 500 µl to 1 ml per 100 square centimeters is applied per application, however, the amount may vary depending on the viscosity of the particular solution of minoxidil and the concentrations of minoxidil and dioxacycloalkane. In general, an amount sufficient to provide a thin coating over the surface of the skin is applied.

The preferred method of treatment of this invention involves the direct application to the skin of a cream, aqueous-organic or organic gel, lotion, spray, solution or aerosol containing both minoxidil and the absorption enhancer dioxacycloalkane compound in the amounts described above. However, each of minoxidil and the absorption enhancer dioxacycloalkane compound can be applied separately, each in admixture with a pharmaceutically acceptable carrier such as water, ethanol or propylene glycol, for example. The order of application may effect the penetration of minoxidil or its effect on hair regrowth. When applied separately, it is preferred that dioxacycloalkane is applied first and the minoxidil is applied shortly thereafter, preferably within about two hours, more preferably within about 60 to about 90 minutes, and most preferably within one hour of application of the dioxacycloalkane. The time period between application of the dicycloalkane and minoxidil is primarily limited by convenience to the user. When the minoxidil and dioxacycloalkane are applied separately each is applied in the amounts discussed above.

Typical gel formulations which may be employed this invention include the following:

| Formula | | Amount (g) |
|---|---|---|
| (A) | Propylene glycol | 98.0 |
|  | Carbopol 940 (B. F. Goodrich) | 2.6 |
|  | Minoxidil | 2.0 |
|  | 2-n-nonyl-1,3-dioxolane | 2.0 |
| (B) | Isopropyl myristate | 92.0 |
|  | Tween 80 | 0.6 |
|  | Aerosil R972 (silica) | 9.0 |
|  | Minoxidil | 2.0 |

| Formula | | Amount (g) |
|---|---|---|
| | 2-n-nonyl-1,3-dioxolane | 5.0 |
| (C) | Isopropanol | 36.0 |
| | Propylene glycol | 27.0 |
| | Water | 27.0 |
| | Hydroxypropylcellulose | 1.0 |
| | Minoxidil | 2.0 |
| | 2-n-nonyl-1,3-dioxolane | 7.0 |
| (D) | Ethanol | 64.4 |
| | Propylene glycol | 18.4 |
| | Water | 9.2 |
| | Hydroxypropylcellulose | 2.0 |
| | Minoxidil | 1.0 |
| | 2-n-nonyl-1,3-dioxolane | 5.0 |
| (E) | Ethanol | 57.4 |
| | Propylene glycol | 16.4 |
| | Water | 8.2 |
| | Hydroxypropylcellulose | 2.0 |
| | Minoxidil | 1.0 |
| | 2-n-nonyl-1,3-dioxolane | 15.0 |
| (F) | Formula (A) through (E), but in place of 2-n-nonyl-1,3-dioxolane, one of the following compounds is used: | |
| | 1) 2-n-pentyl-1,3-dioxolane | |
| | 2) 2-n-heptyl-1,3-dioxolane | |
| | 3) 2-n-undecyl-1,3-dioxolane | |
| | 4) 2-n-nonyl-1,3-dioxolane | |
| | 5) 2-(2',6'-dimethyl-2'-heptaenyl)-1,3-dioxane | |

In the present method for treatment of hair loss, the minoxidil and absorption enhancer dioxacycloalkane compound are each applied at the amounts discussed above, to the area of skin in need of treatment, preferably only once per day. Application of the present method more than one time per day has not been demonstrated to be necessary for either earlier or greater hair growth response. It has been found that the once daily application of minoxidil in combination with the present dioxacycloalkane compound provides more hair regrowth and faster hair regrowth than a once daily application of the same amount of minoxidil in vehicle (Rogaine® TS), other potassium channel opener drugs and androgens, or 5% minoxidil alone (greater than 2× hair growth) and results in significantly more and faster hair regrowth than even a two times daily application of minoxidil and other vehicle. Thus, by use of the present method the amount of minoxidil required for hair regrowth can be significantly reduced and the number of applications per day may be reduced to only one. Moreover, the regrowth of hair begins earlier with the present treatment than with conventional treatments using up to twice as much minoxidil per day.

As noted above, the enhancement of hair growth efficacy of minoxidil (2.5%) by the present method is observed as both an increase in the amount of hair growth in the treated area and the promotion of earlier hair growth compared to treatment with 5% minoxidil alone or Rogaine® TS. Since the follicular target cell(s) for minoxidil as a hair growth agent is not known, it is uncertain whether the improvement in the efficacy of minoxidil when used in combination with the absorption enhancer dioxacycloalkane compound is due solely to penetration enhancement of minoxidil. The enhancer dioxacycloalkane compounds of the present invention are readily mixable with sebum and thus, it is possible that the enhancer compound facilitates targeting of minoxidil to the sebaceous gland of the hair follicle and thereby promotes an earlier and greater hair growth response.

The present hair treatment method may be continued until the desired amount of hair has been regrown in the treated area. A significant regrowth of hair is generally evident by as early as only four weeks after commencement of treatment on a once per day basis. Thus, in general, the present treatment protocol is continued for at least four weeks until the desired effect is achieved. Usually, however, treatment is continued for up to 1 or 2 years or longer to prevent the loss or minimize the loss of hair.

In evaluating the method of the present invention, the efficacy of minoxidil in combination with the dioxacycloalkane compound was tested in vivo using hairless rat skin and a diffusion cell procedure that closely simulates the in vivo situation in that the bald skin is exposed to ambient conditions. A flow-through diffusion cell that perfuses the dermal side of the skin was used. Liquid samples were obtained continuously by automatic collection of the perfusion liquid. The diffusion cell is equipped with a water jacket to provide temperature control and equilibration of the skin sample with the dermal liquid.

The general method used in Examples 1 through 3 of this invention is the following: A skin sample was mounted in the perfusion cell and allowed to equilibrate for five hours at 32° C.±1° C. The water-jacket temperature was adjusted to 37° C. and the liquid in the dermal compartment was diluted bovine albumin in saline water (1.5% w/v). Antibiotics were added to the bathing solution to avoid bacterial contamination. 500 mg of each test drug in a 0.1 ml of ethanol/water (95/5 w/v) mixture was applied to the epidermal surface of the skin sample. After application, the solvent was allowed to evaporate for about one to two hours, leaving a solid drug deposit on the skin sample. The test drug was labelled with a radioactive compound so that its absorption flux could be monitored at hourly intervals during a 48 hour period. After 24 hours following the drug application, 0.1 ml of solution of the enhancer compound was applied to the treated area.

In the in vitro testing using hairless rat skin and isolated human skin, the results of which are described in the example below, the percentage of minoxidil found in the epidermis, the dermis, and the dermal compartment over a 24 hour period were monitored. The amount found in the dermal compartment corresponds to the amount which is totally transmitted through the skin and enters the subdermal body circulatory system. The amount of minoxidil remaining on the skin surface or otherwise loosely held in the epidermis was recovered by washing.

The following examples will serve to illustrate the present invention without being deemed limitative thereof.

In these examples, parts are by weight unless otherwise indicated.

EXAMPLE 1

Three different solutions of minoxidil were prepared in an ethanol-propylene glycol (80:20 on a volume basis) solvent mixture. In solution 1, no dioxolane was used; in each of the other two solutions (2 and 3) there was added 2% (solution 2) and 7% (solution 3) respectively, of 2-n-nonyl-1,3-dioxolane.

| Solution | % Solvent | % Minoxidil | % Dioxolane |
|---|---|---|---|
| 1 | 98 | 2 | 0 |
| 2 | 96 | 2 | 2 |
| 3 | 91 | 2 | 7 |

Each of these solutions was applied to isolated hairless rat skin as described above. After 24 hours the amounts (percent) of minoxidil in the layers of skin were found to be as follows:

TABLE I

| | Solution | | |
|---|---|---|---|
| | 1 | 2 | 3 |
| Dermal Compartment | 0.46 ± 0.76% | 51.43 ± 5.60% | 75.90 ± 3.22% |
| Epidermis | 4.38 ± 1.86 | 11.33 ± 4.48 | 2.29 ± 1.34 |
| Dermis | 2.78 ± 2.03 | 5.74 ± 1.11 | 4.29 ± 1.80 |
| Washings | 88.30 ± 5.54 | 29.05 ± 6.96 | 15.40 ± 1.79 |

These data demonstrate the outstanding effectiveness of the dioxolane compound in enhancing the penetration of minoxidil through the skin.

The minoxidil solutions used in all the examples contained an amount of $^{14}$C-labelled minoxidil. The data are based on radioactive counts.

EXAMPLE 2

Example 1 was repeated utilizing isolated human epidermis in place of the rat skin. The results were as follows (percent minoxidil in each layer):

TABLE II

| | Solution | | |
|---|---|---|---|
| | 1 | 2 | 3 |
| Dermal Compartment | 0.47 ± 0.76% | 6.43 ± 5.73% | 7.35 ± 1.82% |
| Epidermis | 11.76 ± 4.95 | 52.29 ± 8.57 | 49.67 ± 10.27 |
| Washings | 69.52 ± 23.27 | 36.35 ± 6.30 | 29.19 ± 7.21 |

These data confirm the effectiveness of dioxacycloalkanes as absorption enhancers on human skin as well as on rat skin when used with minoxidil.

EXAMPLE 3

This example compare treatment of monkey skin with a solution of minoxidil and 2-n-nonyl-1,3-dioxolane with treatment using minoxidil alone.

Minoxidil was synthesized and purified at The Upjohn co. 2-n-nonyl-1,3-dioxolane (n-DIOX) was obtained from Macrochem Corp. (Billerica, Mass.). Rogaine® TS was prepared at The Upjohn Co. and consisted of 2% minoxidil (weight/volume) dissolved in a carrier of 20% propylene glycol, 60% ethanol and 20% water. The minoxidil-(n-DIOX) formulation was also prepared at The Upjohn Co. and contained 2.5% minoxidil (weight/volume) in a carrier of 10% (n-DIOX), 25% propylene glycol and 65% isopropyl alcohol. Since topical 2.5% minoxidil in 10% (n-DIOX) was well tolerated in balding human volunteers and yielded steady state serum levels of drug comparable to that associated with topical 5% minoxidil in a propylene glycol, ethanol and water carrier, the 2.5% minoxidil-(n-DIOX) formulation was selected for use. Approximately 250 µl of carrier alone or drug (prepared in carrier) were topically applied via a paintbrush to a 1 in$^2$ tattooed area in the center of the balding scalp, 5 days/week, Monday–Friday, for 16 weeks. Topical dosing was carried out between 6 AM and 7 AM. In the b.i.d. (twice per day) treated groups, the second dose was administered between 4 PM and 5 PM. The dosed site was monitored daily for evidence of irritation. Physical or behavioral changes were also recorded on a daily basis.

Experimental Groups—Monkeys were assigned to groups on the basis of the weight of scalp hair prior to treatment. Hair was collected 4 weeks prior to the start of dosing and weighed. This procedure insured that the mean pretreatment hair weight for each group was similar. Monkeys were placed into one of the following 8 groups: q.d. (treatment once per day) Rogaine® plus carrier (n=5), q.d. Rogaine® TS (n=5), b.i.d. (twice per day) Rogaine® plus carrier (n=5), b.i.d. Rogaine® TS (n=5), q.d. 10% (n-DIOX) plus carrier (n=5), q.d. 2.5% minoxidil in 10% (n-DIOX) plus carrier (n=5), b.i.d. 10% (n-DIOX) plus carrier (n=5) and b.i.d. 2.5% minoxidil in 10% (n-DIOX) vehicle (n=5). Groups receiving carrier alone or n-DIOX plus carrier without minoxidil served as negative controls. Each monkey was treated with about 250 µl of the appropriate solution per 1 in$^2$ area of the scalp.

Method of Scald Hair Collection—Stimulatory effects of minoxidil on scalp hair growth in stumptail macaques were assessed by weighing the hair from the topically dosed 1 in$^2$ area in the center of the balding scalp. Briefly, hair collections were performed by sedating each monkey and shaving the tattooed area with a model 8900 Wahl clipper (Wahl Clipper Co., Sterling, Ill.) while collecting the hair through a vacuum line into 50% ethanol. Each hair sample was aspirated onto preweighed Whatman glass microfiber filter paper (Whatman International Ltd., Maidstone, England), dried for 24 hours in a 40° C. oven and weighed on a Mettler AE 200 automatic tare analytical balance (Mettler Instruments Co., Hightstown, N.J.). At baseline (week O) and at 4 week intervals during the 16 week study, scalp hair weight data (mg/in$^2$) were expressed as the change in weight compared to baseline. Cumulative change in hair weight (sum of the 4 week changes in hair weight) was also obtained for the 16 week study. Body weight (kg) of each monkey was measured at each 4 week hair collection to monitor health.

Urine Collection—At steady state (after 4 consecutive days of dosing), 24 hour urine samples were collected from all q.d. and b.i.d. minoxidil-treated monkeys via metabolism cages. Each monkey was placed in a metabolism cage immediately after application of the first dose of drug on the 4th day of the week. The second dose was applied to the scalp of b.i.d. treated animals in the metabolism cage as described above. Each 24 hour urine volume was recorded and aliquots were frozen at −78° C. Urine was analyzed by HPLC, described below, to assess urinary excretion of topically applied minoxidil.

Extraction and HPLC Analysis of Total Urinary Minoxidil (Parent Drug and Glucuronide—To a 1.0 ml sample of urine from each monkey, 100 µl of Glucurase® (Sigma, St. Louis, Mo.) was added and mixed thoroughly in glass test tubes. Tubes were placed in a shaking water bath (37° C.) for 16 hours, removed and allowed to cool to room temperature. Each urine sample was applied to a ChemElut™ CE1001 1.0 ml column (Varian, Harbor City, Calif.) and allowed to absorb for 3 min. Total minoxidil was eluted off the column with three 4.0 ml applications of 10% 1-butanol in ethyl acetate. The eluates were collected into tubes and the solvent removed under reduced pressure with a Vortex Evaporator (Buchler Instruments, Fort Lee, N.J.). A 1.0 ml Bond Elut™ non-encapped CN column (Varian, Harbor City, Calif.) was prewashed with 1.0 ml methanol followed by 1.0 ml water. The dried urinary residue of each sample from the ChemElut™ column was resuspended in 1.0 ml of 0.1% acetic acid in water and added to the pre-rinsed CN column at 0.5 ml/min. The sample tube was rinsed with 1.0 ml 0.1% acetic acid and the rinse added to the column. The column was washed consecutively with 2.0 ml each of water, ethyl acetate, chloroform and acetonitrile followed by 1.0 ml water. The column was allowed to dry under reduced pressure for 1 min. Total minoxidil was eluted from the column with mobile phase, described below, and collected into injection vials for HPLC analysis.

Coupled analytical columns, a Widepore C8, 4.6×100 mm (5 μm) (JT Baker, Phillipsburg, N.J.) followed by two 3×3 CR18 (3 μm) (Perkin-Elmer, Norwalk, Conn.), were used for the detection of total minoxidil under isocratic HPLC conditions. An RP-300 C8 (7 μm) guard column (Brownlee Labs, Santa Clara, Calif.) was used prior to the analytical columns. The mobile phase consisted of 15% acetonitrile in water containing 0.1% trifluoroacetic acid at a flow rate of 1.0 ml/min. The sample injection volume was 100 μl. The column effluent was monitored at 280 nm UV. Standards were prepared by spiking 1.0 ml aliquots of urine from carrier-treated monkeys with minoxidil. Urine concentrations of total minoxidil were determined by linear regression standard curve analysis utilizing the integrated area under the curve for the standards extracted and isolated as described above. Urinary data were expressed as total minoxidil (μg) excreted in the 24 hour collection period. HPLC data were collected and interpreted with a Spectra-Physics Analytical Spectra-Station™ (Spectra-Physics, Inc., San Jose, Calif.) software system.

Statistics—All data (body weight, hair weight and urine and levels of total minoxidil) of each group were expressed as mean ± SEM. Body weight data (baseline compared to the mean of measurements of weeks 4 through 16) were analyzed by the nonparametric Wilcoxon sign rank test for paired data (two-tailed). An ANOVA was performed on the ranks of the hair weight data to show overall differences among groups. Group pair-wise comparisons for the hair weight data were made by the nonparametric Wilcoxon rank sum test (two-tailed) at each 4 week hair collection and for the entire study (cumulative change in hair weight). Levels of total minoxidil in the urine were subjected to log transformation and analyzed by the same methods used for the hair weight data. Changes were considered marginally significant at $p<0.10$ and significant at $p<0.05$.

Body Weight and Gross Observations—There were no significant changes in body weight (baseline compared to treatment) in almost all q.d. and b.i.d. minoxidil and carrier-treated groups of monkeys. However, a slight but statistically significant increase in body weight occurred in the q.d. (n-DIOX) carrier group (baseline=7.9±0.6 kg vs. treatment= 8.4±0.5 kg, $p<0.05$). After approximately 4 weeks of dosing and throughout the remainder of the 16 week study, most q.d. and b.i.d. drug and vehicle-treated monkeys displayed dry skin in the tattooed region of the scalp. Skin dryness tended to be more severe in the b.i.d. treatment groups. Despite persistent dryness of the scalp skin, minimal exfoliation was observed during the monthly hair collections. This observation was confirmed by the absence of sloughed skin on the glass microfiber paper used to filter the hair. Thus, weight of scalp hair was probably not influenced by sloughed skin. Erythema, hemorrhage or any other form of irritation were not detected in the dosed area of any minoxidil or carrier-treated monkey. Physical or behavioral changes were not observed in any monkeys.

Scald Hair Weight—Table I presents the scalp hair weight data expressed as the change from baseline at 4 week intervals for vehicle and minoxidil-treated groups of monkeys.

TABLE I

| | Change From Baseline of Scalp Hair Weight (mg/in$^2$) Associated With Carrier and Minoxidil Treatment | | | | | | | |
|---|---|---|---|---|---|---|---|---|
| Time (Weeks) | Q.D. Rogaine® Carrier | Q.D. Rogaine® TS | B.I.D. Rogaine® Carrier | B.I.D. Rogaine® TS | Q.D. (n-DIOX) Carrier | Q.D. Minoxidil (n-DIOX) | B.I.D. (n-DIOX) Carrier | B.I.D. Minoxidil (n-DIOX) |
| 4 | 0.2 ± 0.4 | 0.2 ± 0.1 | 0.8 ± 0.8 | 0.0 ± 0.3 | 0.9 ± 0.3 | 3.5 ± 0.5 | 0.3 ± 0.1 | 3.1 ± 0.6 |
| 8 | −0.9 ± 0.4 | 2.2 ± 0.7 | 0.1 ± 0.2 | 3.9 ± 1.4 | 0.5 ± 0.5 | 7.1 ± 1.6 | 0.5 ± 0.7 | 9.1 ± 2.0 |
| 12 | −0.5 ± 0.3 | 2.3 ± 0.4 | 0.1 ± 0.2 | 5.1 ± 1.4 | 0.3 ± 0.6 | 5.6 ± 0.9 | 0.4 ± 0.4 | 7.8 ± 1.3 |
| 16 | 0.3 ± 0.6 | 3.5 ± 0.7 | 4.3 ± 1.2 | 1.3 ± 0.4 | 1.3 ± 0.4 | 7.9 ± 0.8 | 2.2 ± 1.1 | 6.4 ± 2.0 |

Data are mean ± SEM

Relevant pairwise comparisons and levels of significance for the data from Table I are shown in Table 2 below. At week 4, q.d. and b.i.d. minoxidil-(n-DIOX) treatments elicited a significant increase in hair weight compared to their respective carriers whereas neither q.d. or b.i.d. Rogaine® TS treatments caused stimulation of hair growth. Thus, the present method results in an earlier hair regrowth than treatment with as much as twice as much minoxidil but using a different carrier. All q.d. and b.i.d. drug-treated groups of monkeys displayed a substantial elevation in hair weight, compared to their respective carriers, at weeks 8, 12 and 16. At week 8, q.d. and b.i.d. minoxidil-(n-DIOX) groups grew significantly more hair than q.d. and b.i.d. Rogaine® TS, at weeks 12 and 16. Twice daily application of Rogaine® TS failed to produce significantly greater weight of hair, compared to once daily administration of the same formulation at any time point. Similarly, the efficacy of b.i.d. and q.d. minoxidil-(n-DIOX) was comparable.

FIG. 1 illustrates the cumulative change in scalp hair weight over the entire study for carrier and drug-treated groups of monkeys. All q.d. and b.i.d. drug treatments evoked marked augmentation of hair weight relative to their respective carriers. Once and twice daily administration of minoxidil-(n-DIOX) generated significantly greater hair weight compared to q.d. and b.i.d. application of Rogaine® TS, respectively. Statistically significant differences in cumulative hair weight were not evident between q.d. and b.i.d. Rogaine® TS-treated groups or between q.d. and b.i.d. minoxidil-(n-DIOX) treated groups.

Steady State Urinary Excretion of Total Minoxidil—Table 3 shows steady state levels of total urinary minoxidil. Once per day administration of minoxidil-n-DIOX tended to produce higher urinary level of total minoxidil compared to q.d. application of Rogaine® TS. However, the increase was not statistically significant due to excessive variability in the former group. Monkeys treated with b.i.d. minoxidil-n-DIOX displayed significantly greater urinary excretion of total minoxidil compared to b.i.d. application of Rogaine® TS.

TABLE III

| Treatment Group | Steady State Urinary Excretion of Total Minoxidil |
|---|---|
| | Total Urinary Minoxidil (μg) |
| Q.D. Rogaine ® TS | 384 ± 93 |
| Q.D. Minoxidil-(n-DIOX) | 459 ± 209 (NS)[a] |
| B.I.D. Rogaine ® TS | 314 ± 89 |
| B.I.D. Minoxidil-(n-DIOX) | 888 ± 82 (0.01)[b] |

[a]NS = not significant vs. Q.D. Rogaine ® TS
[b]vs. B.I.D. Rogaine ® TS
Data are mean ± SEM The 2.8 fold elevation in urinary excretion of total minoxidil elicited by twice daily application in combination with 10% (n-DIOX) coincided with that observed to be generated by b.i.d. administration of the same formulation of androgenic alopecia patients. Additional data to support the penetration enhancement properties of (n-DIOX) with respect to topical minoxidil were derived from clinical studies in which steady state serum levels of total minoxidil were elevated 2.5 fold by 10% (n-DIOX) compared to Rogaine® TS in balding human male patients.

What is claimed is:

1. A method for treating hair loss resulting from alopecia which comprises topically applying to skin at a desired area for hair regrowth, no more than once daily, a composition comprising a pharmaceutically effective amount, in the range of 0.5 to 3% by weight, of minoxidil, and a non-toxic penetration enhancing effective amount, in the range of 2 to 15% by weight, of a 1,3-dioxolane compound of formula (III)

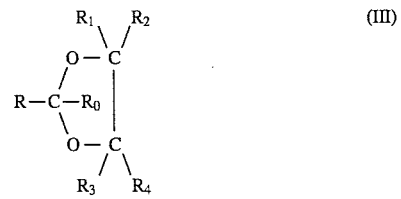

wherein R represents a $C_7$ to $C_{10}$ alkyl group, $R_0$ represents hydrogen and $R_1$, $R_2$, $R_3$ and $R_4$ each, independently, represent hydrogen or $C_1$ to $C_4$ alkyl, wherein the minoxidil and 1,3-dioxolane are applied in a cosmetically acceptable aqueous carrier comprising lower alkanol and lower alkyl glycol.

* * * * *